(12) United States Patent
Villinger et al.

(10) Patent No.: US 12,117,430 B2
(45) Date of Patent: Oct. 15, 2024

(54) DEVICE AND METHOD FOR PARTIAL TRANSFER OF A LIQUID SAMPLE, COMPRISING MULTIPLE COMPONENTS AND METHOD FOR THE ONLINE DETERMINATION AND ANALYSIS OF THESE COMPONENTS

(71) Applicant: V&F Analyse—Und Messtechnik GmbH, Absam (AT)

(72) Inventors: Johannes Villinger, Innsbruck (AT); Werner Federer, Absam (AT)

(73) Assignee: V&F Analyse-Und Messtechnik GmbH, Absam (AT)

( * ) Notice: Subject to any disclaimer, the term of this patent is extended or adjusted under 35 U.S.C. 154(b) by 1159 days.

(21) Appl. No.: 16/624,572

(22) PCT Filed: Jun. 18, 2018

(86) PCT No.: PCT/EP2018/066128
§ 371 (c)(1),
(2) Date: Jul. 22, 2020

(87) PCT Pub. No.: WO2018/234245
PCT Pub. Date: Dec. 27, 2018

(65) Prior Publication Data
US 2020/0355661 A1    Nov. 12, 2020

(30) Foreign Application Priority Data
Jun. 19, 2017  (EP) ..................... 17176687

(51) Int. Cl.
*G01N 33/00*   (2006.01)
*G01N 1/10*    (2006.01)
(Continued)

(52) U.S. Cl.
CPC .......... *G01N 33/0011* (2013.01); *G01N 1/10* (2013.01); *G01N 1/22* (2013.01); *G01N 1/28* (2013.01); *G01N 33/0073* (2013.01)

(58) Field of Classification Search
CPC ........ G01N 33/0011; G01N 1/10; G01N 1/22; G01N 1/28; G01N 33/0073;
(Continued)

(56) References Cited

U.S. PATENT DOCUMENTS 5,454,274 A * 10/1995 Zhu ..................... H01J 49/04
                                                250/288
9,562,430 B1    2/2017 Monteiro
(Continued)

FOREIGN PATENT DOCUMENTS

CN   101713712 A   5/2010
CN   105590827 A   5/2016
(Continued)

OTHER PUBLICATIONS

International Application No. PCT/EP2018/066128, "International Preliminary Report of Patentability and Written Opinion", mailed Jan. 2, 2020, 9 pages.
(Continued)

*Primary Examiner* — Robert R Raevis
(74) *Attorney, Agent, or Firm* — COZEN O'CONNOR

(57) ABSTRACT

The invention relates to a device and method for partial conversion of a fluid sample comprising a plurality of components and a process for on-line determination and analysis of components of a fluid sample comprising a plurality of components. The invention also relates to the use of the device as a sample treatment device.

18 Claims, 6 Drawing Sheets

Figure 1:
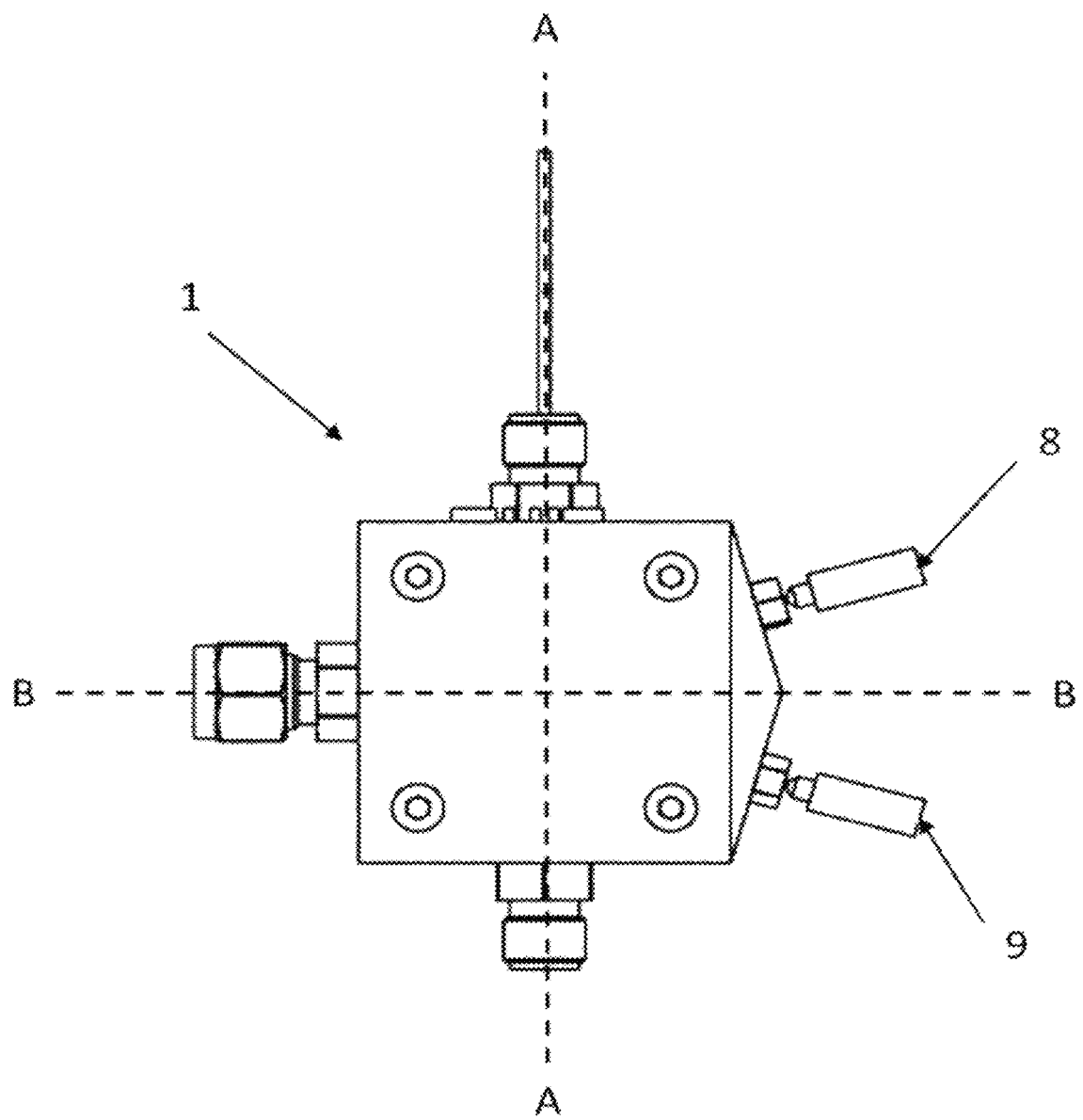

(51) Int. Cl.
*G01N 1/22* (2006.01)
*G01N 1/28* (2006.01)

(58) Field of Classification Search
CPC .... G01N 33/0016; G01N 1/44; G01N 1/4022; G01N 7/16; G01N 2035/00356; G01N 5/04; G01N 2030/126; B01D 5/006; B01D 19/0036; H01J 49/049; B01B 1/005

USPC ............... 73/864.81, 31.07, 863.11, 863.12; 422/530
See application file for complete search history.

(56) References Cited

U.S. PATENT DOCUMENTS

| | | |
|---|---|---|
| 2010/0122564 A1 | 5/2010 | Crosson et al. |
| 2014/0084154 A1 | 3/2014 | Bazhenov et al. |
| 2014/0329333 A1 | 11/2014 | Nagy et al. |

FOREIGN PATENT DOCUMENTS

| | | | |
|---|---|---|---|
| DE | 102011081287 | | 2/2013 |
| JP | S49-002385 A | | 1/1974 |
| JP | S58-62248 A | * | 4/1983 |
| JP | 2010529480 A | * | 8/2010 |

OTHER PUBLICATIONS

International Application No. PCT/EP2018/066128, "International Search Report", mailed Sep. 13, 2018, 4 pages.

* cited by examiner

DEVICE AND METHOD FOR PARTIAL TRANSFER OF A LIQUID SAMPLE, COMPRISING MULTIPLE COMPONENTS AND METHOD FOR THE ONLINE DETERMINATION AND ANALYSIS OF THESE COMPONENTS

The invention relates to a device and method for the partial conversion of a fluid sample comprising a plurality of components and a method for on-line determination and analysis of components of a fluid sample comprising a plurality of components. The invention also relates to the use of the device as a sample preparation device.

Technical process plants in the chemical industry as well as in the pharmaceutical industry for the production of various products and medicines, but also purification plants for water or solvents, are currently monitored on-line via simple and integral process parameters such as pressure, temperatures or light absorption etc. by means of specific sensors. However, differential reactions in these systems, such as the formation of by-products, are only detected during off-line product control, which is carried out in a laboratory process. For instance, the formation of by-products such as diacetyl in beer fermentation or azotoluidine in protein separation columns as well as the formation of toxins in other processes should be mentioned here.

As another example of undesirable processes, engine oil dilution processes in combustion engines, especially in internal combustion engines in motor vehicles, should be mentioned. The engine oil in an internal combustion engine can be diluted with ethanol-containing fuel, for example Super E10, or biodiesel-containing diesel fuel, which may significantly change the lubricating properties of the engine oil. These changes in the properties of the engine oil may have a negative effect on the internal combustion engine and may cause damage to the internal combustion engine.

Due to increasing pressure to optimize and to higher quality demands on the process plants, higher demands are made with respect to the monitoring of the above-mentioned undesirable side reactions and the possible formation of undesirable impurities in the products. The products or impurities formed from possible side reactions may be liquid or gaseous.

In the detection of gaseous compounds, gas phase measuring instruments such as flame ionisation detectors, fluorescence measuring instruments and mass spectrometers have established themselves as the most sensitive and fastest detection systems.

Nevertheless, the problem remains that undesired and/or toxic by-products can arise undetected in processes and cannot be detected immediately or within a short time. The same is true for undesirable secondary processes, such as the engine oil dilution mentioned above. In the prior art, samples are often taken at regular intervals or even randomly, which are then usually sealed or treated otherwise before they can be analysed in a laboratory. However, this process sometimes results in large delays between sampling and obtaining the analysis result in the laboratory. This poses the problem that it is not possible to react immediately to the formation of undesirable and/or toxic by-products in the process. Such processes, wherein the sample is taken and then examined in a laboratory, can therefore also be referred to as "off-line processes".

It can also be time-consuming in the analysis of liquid samples if the undesired by-products or impurities in the sample, too, are present in the liquid state. There is therefore a need for suitable and improved devices for the on-line preparation and analysis of such samples.

It is therefore a task of the present invention to provide a device for the partial conversion of a liquid sample comprising a plurality of components to the gas phase which avoids the disadvantages of known devices according to prior art.

Furthermore, the task of the present invention is to provide a method for the partial conversion of a liquid sample comprising a plurality of components to the gas phase which avoids the disadvantages of known devices according to prior art.

A further task of this invention is to provide a method for on-line determination and analysis of components of a liquid sample comprising a plurality of components, which allows rapid detection and analysis of liquid samples.

The invention is based on the finding that the above-mentioned tasks are solved with the aid of a chamber in which an equilibrium between the gas and liquid phases of a liquid sample introduced into the chamber is quickly established at a given temperature, i.e. within 30 seconds, or within 20 seconds, or within 10 seconds.

The invention therefore provides a device for the partial conversion of a liquid sample comprising a plurality of components to the gas phase, which comprises (a) a heatable chamber in which a two-phase or multi-phase gas/liquid system is produced, which has
  (a1) a liquid inlet port for the supply of the liquid sample,
  (a2) a liquid outlet port for the discharge of liquid components which have not been converted to the gas phase, and
  (a3) has a gas phase outlet port for the discharge of the generated gas phase from the chamber, and (b) a device for controlling the flow rate of the liquid sample into the liquid inlet port from 1 µl/min to 3000 µl/min.

The device according to the invention has the advantage that the device can be connected directly to a process to be monitored, such as a work or production process. Here, the advantage is that the device according to the invention can be used "on site", in particular for treatment and preparation of samples taken from the process to be monitored. Therefore, the liquid sample to be examined and analysed can be taken directly from such a process, for instance from a reactor, a pipeline or a container of this process, introduced into the device according to the invention and treated or prepared there.

The device according to the invention therefore allows on-line sample preparation and on-line sample treatment of liquid samples taken directly from a process in an advantageous way, in particular for a downstream analysis device, such as a mass spectrometer.

For the purposes of this application, 'on-line' means that the total time from taking the liquid sample from a process until obtaining the result of the analysis of the liquid sample from an analysis device is less than 5 minutes, preferably less than 3 minutes and more preferably less than 1 minute. This means that the liquid sample taken directly from a process can be analysed virtually in "real time".

"On-line" also means that the liquid sample is both taken from the process to be monitored and is also analysed "on site". In other words, the liquid sample is taken directly, i.e. via a fluid connection, from the process, is introduced into the device according to the invention, where it is prepared and/or treated, and is then optionally analysed in a downstream analysis device such as a mass spectrometer.

A further advantage of the device according to the invention is that the device only takes small volumes of the liquid sample from the process to be monitored, the volumes being in the range of 10 µl to 400 µl. The extraction of such small volumes does not influence the process to be monitored.

Without wanting to be bound to theory, an equilibrium is created in the device according to invention according to the laws of thermodynamics in that, in a solution at a defined temperature and pressure, liquid components develop corresponding partial pressures above the liquid solution which are proportional to the concentrations of the components in the liquid phases. Thus, a gas/liquid two-phase or multi-phase system is created, which is in equilibrium. In other words, the plurality of components of the liquid sample are partially converted to the gas phase according to their concentrations in the liquid phase of the liquid sample.

A further advantage of the device according to the invention is that the components of the liquid sample converted to the gas phase are only present in low concentrations in the gas phase, and therefore no further possible reactions between the components can occur in the gas phase. Therefore, if necessary, the gaseous components may also be transported over long distances to the downstream analysis device, such as a mass spectrometer, without changing the concentrations of the components in the extracted gas phase.

The device according to the invention, as described here in all embodiments, can therefore also be described as a partial pressure generator.

The two-phase or multi-phase gas/liquid system, as described above, is reached in the chamber. The liquid phase or liquid phase of this two-phase or multi-phase system can be single-phase, two-phase or multi-phase.

The chamber in which the two-phase or multi-phase gas/liquid system is reached is located inside the device and can generally take different shapes. The chamber has an upper and a lower region, the lower region being connected to the upper region and the upper and lower regions merging into each other. Preferably the upper region of the chamber has the shape of a solid of revolution with constant diameter, and the lower region of the chamber has the shape of a solid of revolution with decreasing diameter.

Preferably, the solid of revolution with constant diameter has the shape of a cylinder, and the solid of revolution with decreasing diameter has the shape of a cone or a truncated cone. The diameter of the cylinder preferably corresponds to the diameter of the base area of the cone or truncated cone, i.e. the base area of the cylinder is also the base area of the cone or truncated cone.

In a preferred embodiment of the chamber, the upper region has the shape of a cylinder and the lower region has the shape of a cone, the diameter of the cylinder corresponding to the diameter of the base area of the cone, the liquid outlet port being located at the tip of the cone. This ensures that the liquid phase of the two-phase or multi-phase gas/liquid system passes quickly and efficiently through the liquid outlet port and can be extracted from the chamber or device.

If the upper region of the chamber is a solid of revolution of constant diameter or if the upper region of the chamber is in the shape of a cylinder, the diameter of the solid of revolution or of the cylinder is preferably between 6 mm and 24 mm, more preferably between 8 mm and 22 mm, yet more preferably between 10 and 20 mm, and most preferably between 12 and 18 mm.

If the lower region of the chamber is a solid of revolution of decreasing diameter or if the lower region of the chamber is in the shape of a cone or truncated cone, the diameter of the base of the solid of revolution or of the cone or truncated cone is preferably between 6 mm and 24 mm, more preferably between 8 mm and 22 mm, yet more preferably between 10 and 20 mm, and most preferably between 12 and 18 mm.

The diameter of the solid of revolution with a constant diameter or of the cylinder preferably corresponds to the diameter of the base of the solid of revolution with a decreasing diameter or of the cone or truncated cone.

The height of the chamber means the longest distance between an upper end of the upper region and the lower end of the lower region. If the upper region of the chamber is cylindrical in shape and the lower region is conical in shape, the height of the chamber is the distance between the top surface of the cylinder and the tip of the cone, measured perpendicular to the top surface of the cylinder.

The chamber preferably has a height between 4 mm and 30 mm, more preferably between 6 mm and 28 mm, yet more preferably between 9 mm and 26 mm, yet more preferably between 12 mm and 24 mm, and most preferably between 18 mm and 22 mm.

Preferably, the chamber has a volume of 0.1 to 25 cm3, more preferably from 0.5 to 20 cm3, yet more preferably from 0.75 to 15 cm3, yet more preferably from 1 to 10 cm3 and most preferably from 2 to 8 cm3.

The liquid sample is introduced into the chamber through the liquid inlet port for the liquid sample inlet. The liquid inlet port for the liquid sample inlet is preferably located in the lower region of the chamber, more preferably at or near the transition between the upper and lower regions of the chamber.

The device for controlling the flow rate of the liquid sample into the liquid inlet port preferably comprises a dosing valve, more preferably a spindle valve. Further preferably, this device consists of a valve, more preferably it consists of a spindle valve. By means of this device, the flow rate of the liquid sample into the liquid inlet port of the chamber is controlled. The flow rate is preferably 2 to 2000 µl/min, more preferably 5 to 1750 µl/min, yet more preferably 10 to 1500 µl/min, yet more preferably 20 to 1000 µl/min, and most preferably 50 to 500 µl/min.

Liquid components of the liquid sample that have not been converted to the gas phase are led out of the chamber through the liquid outlet. Preferably the liquid outlet port for the discharge of liquid components not converted to the gas phase is located in the lower region of the chamber, more preferably at the lowest end of the lower region of the chamber. The liquid outlet port is therefore preferably located at the tip of the cone or in the top surface of the truncated cone. A pump, such as a peristaltic pump, may be used to draw the liquid out of the chamber more quickly and completely through the liquid outlet port.

The components converted to the gas phase are led out of the chamber through the gas phase outlet port. The gas phase outlet port is located in the upper region of the chamber, more preferably in the upper half of the upper region of the chamber.

The gas phase outlet port is preferably connected to an analysis device. The analysis device is preferably a mass spectrometer, in particular a mass spectrometer suitable for the analysis of gaseous components. For this invention, commercially available mass spectrometers or mass spectrometers known in prior art, for example from EP 0 290 711, EP 0 290 712, DE 196 28 093 and WO 02/058106, may be used.

The connection between the gas phase outlet and the analysis device is preferably a fluid connection. The fluid connection is preferably a capillary, a tube, a hose or combinations thereof.

Preferably, the device comprises a device for controlling the gas phase flow from the gas phase outlet port from 10 ml/min to 500 ml/min, more preferably 30 ml/min to 400 ml/min, yet more preferably 50 ml/min to 300 ml/min, yet more preferably 70 ml/min to 250 ml/min, and most preferably 100 ml/min to 200 ml/min. The device for controlling the gas phase flow from the gas phase outlet port preferably comprises a valve or consists of a valve.

The chamber inside the device can be heated to reach an adjustable temperature inside the chamber. Preferably, the device has at least one heating element, more preferably at least two heating elements, and heating of the chamber is effected via the walls delimiting the chamber. Preferably, the heating element here is a heating cartridge. The heating element is used to heat the walls delimiting the chamber from the outside.

Preferably, the temperature at the warmest position of the walls delimiting the chamber is at a maximum of 300° C., more preferably at a maximum of 275° C., yet more preferably at a maximum of 250° C., yet more preferably at a maximum of 225° C., yet more preferably at a maximum of 200° C., yet more preferably at a maximum of 175° C., and most preferably at a maximum of 150° C.

Preferably, the temperature at the warmest position of the walls delimiting the chamber is at a minimum of 20° C., more preferably at a minimum of 25° C., yet more preferably at a minimum of 30° C., yet more preferably at a minimum of 35° C., yet more preferably at a minimum of 40° C., and most preferably at a minimum of 45° C.

Preferably, the chamber is heated in such a way that a temperature gradient is generated from the upper region to the lower region of the chamber. This can be achieved, for instance, by positioning the heating element at or near the top of the chamber. This results in a temperature gradient in the chamber, with the temperature in the upper range being higher than that in the lower range. The temperature difference between the warmest part of the upper range and the coolest part of the lower range of the chamber is preferably a maximum of 50° C., more preferably a maximum of 40° C., yet more preferably a maximum of 30° C., yet more preferably a maximum of 20° C., and most preferably a maximum of 10° C.

If two, three or more heaters are used, one heater is positioned at or near the top of the chamber, as described above, and the other heaters are positioned around the walls delimiting the chamber.

Preferably the walls delimiting the chamber comprise a metallic material. Metallic materials are preferred because they have good thermal conductivity, which means that not only heat conduction from the heating element to the walls delimiting the chamber but also heat conduction from the walls to the liquid sample inside the chamber is rapid. Time of the creation of the gas-liquid equilibrium in the chamber can be influenced by suitable selection of the metallic material. The higher the thermal conductivity of the metallic material, the faster the gas-liquid equilibrium in the chamber can be created. Therefore, the metallic materials preferably comprise iron, steel, stainless steel, aluminium, copper, silver and their alloys, more preferably stainless steel. In a preferred embodiment, the metallic materials consist of iron, steel, stainless steel, aluminium, copper, silver as well as their alloys; more preferably, the metallic material consists of stainless steel.

Preferably, the chamber comprises a further liquid inlet port for the insertion of a diluent liquid. The liquid inlet port for introducing a diluent liquid is preferably located in the lower region of the chamber, more preferably at or near the transition between the upper and lower regions of the chamber. Preferably, the liquid inlet port for introducing a diluent liquid is located in the same plane, i.e. the same height or level, of the chamber as the liquid inlet port for the liquid sample inlet.

The diluent liquid is used to dilute the liquid sample in the chamber. The diluent liquid is preferably the "zero substance", i.e. the main component of the liquid sample, as described herein. This additional insertion of the main component into the chamber increases the concentration of the main component in the liquid sample in the chamber and simultaneously reduces the concentration of one or more secondary components in the liquid sample in the chamber. This is particularly advantageous when the original concentration of one or more secondary components in the liquid sample is too high, which can lead to errors in the analysis and quantitative determination of the secondary components. For the purposes of this application, initial concentration means the concentration of the main and secondary components in the liquid sample prior to any dilution, for example by diluent liquids and/or (carrier) gases. In other words, the original concentration corresponds exactly to the concentration of the liquid sample as it was extracted, for instance, from another process or container.

The device preferably further comprises a device for controlling the flow rate of the diluent liquid into the liquid inlet port for inserting a diluent liquid. This device preferably comprises a dosing valve, for example a spindle valve; more preferably this device consists of a spindle valve. The flow rate is preferably 1 to 3000 µl/min, more preferably 2 to 2000 µl/min, yet more preferably 5 to 1750 µl/min, yet more preferably 10 to 1500 µl/min, yet more preferably 20 to 1000 µl/min, and most preferably 50 to 500 µl/min.

Instead of the diluent liquid, other liquids may also be inserted through the liquid inlet port for insertion of a diluent liquid. For instance, a defined reference solution may be inserted to determine the zero point of a downstream analysis device. However, one or several calibration solutions, i.e. solutions with components of known concentrations, may also be inserted in order to calibrate the device and/or the downstream analysis device.

Preferably, the liquid inlet port for the supply of the liquid sample into the chamber and/or the liquid inlet port for insertion of a diluent liquid into the chamber is located in the lower region of the chamber, more preferably at or near the transition between the upper and lower regions of the chamber.

Preferably, the chamber further comprises a gas inlet port for the feeding of gases into the chamber. The gas inlet port is preferably located in the upper region of the chamber, more preferably in the upper half of the upper region of the chamber. Preferably, the gas inlet port is on the same level as the gas phase outlet port, more preferably the gas inlet port is on the same level as the gas phase outlet port and is opposite the gas phase outlet port in the chamber.

Carrier gas can be introduced into the chamber through the gas inlet port. The carrier gas is preferably an inert gas such as $N_2$, Ar or dried air, in particular preferably $N_2$. The carrier gas is used to purge the chamber, especially before commissioning the chamber, in order to remove moisture from the chamber.

Preferably, the chamber further comprises a device for controlling the flow rate of gases into the gas inlet port for feeding gases into the chamber. The flow rate is preferably 50 ml/min to 1000 ml/min, more preferably 100 ml/min to 900 ml/min, yet more preferably 200 ml/min to 800 ml/min, and most preferably 300 ml/min to 600 ml/min.

Preferably, the chamber further comprises a gas outlet port for the outlet of carrier gas from the chamber. The carrier gas can escape from the chamber through the gas outlet port when the chamber is purged, as described above. The gas outlet port is preferably located in the upper region of the chamber, more preferably on the same level, i.e. the same height, of the chamber as the gas inlet port.

The gas phase outlet port for the discharge of the generated gas phase from the chamber and/or the gas inlet port for the feed of gases into the chamber and/or the gas outlet port for the discharge of carrier gas from the chamber are preferably located in the upper half of the upper region of the chamber, more preferably in the upper third of the upper region of the chamber.

In a preferred embodiment of the device, the gas phase outlet port for the discharge of the generated gas phase from the chamber and the gas inlet port for the feed of gases into the chamber and the gas outlet port for the discharge of carrier gas from the chamber are located in the upper half of the upper region of the chamber, more preferably in the upper third of the upper region of the chamber.

Method for Partial Conversion

The present invention also relates to a process for the partial conversion of a liquid sample comprising a plurality of components to the gas phase comprising the steps of:
a) introducing the fluid sample comprising a plurality of components into a heatable chamber of a device,
b) partially converting of the liquid sample to the gas phase so that a gas/liquid two-phase or multi-phase system is created in the chamber, and
c) extracting of the gas phase of the gas/liquid two-phase or multi-phase system from the chamber through a gas phase outlet port of the chamber.

All embodiments of the device according to the invention as described above are also preferred embodiments of the device used in the method according to the invention for the partial conversion of a liquid sample comprising a plurality of components to the gas phase.

In particular, the heatable chamber of the method according to the invention is preferably designed as described above in all embodiments of the device. More preferably, a device comprising the heatable chamber as described above in all embodiments of the device is used in the method according to the invention for the partial conversion of a liquid sample comprising a plurality of components to the gas phase.

The advantages of the device according to the invention described above apply analogously to the method according to the invention.

The liquid sample comprising a plurality of components is introduced into a heatable chamber of the device in step a) preferably via the liquid inlet port for the liquid sample inlet, as described above.

The temperature of the liquid sample before introducing in step a) is preferably 20° C. to 120° C., more preferably between 25° C. and 90° C., and yet more preferably between 30° C. and 70° C.

Preferably, the liquid sample is introduced into the chamber in step a) with a flow rate of 1 µl/min to 3000 µl/min, more preferably from 2 µl/min to 2000 µl/min, yet more preferably 5 µl/min to 1750 µl/min, yet more preferably 10 µl/min to 1500 µl/min, yet more preferably 20 µl/min to 1000 µl/min, and most preferably 50 µl/min to 500 µl/min.

The liquid sample is introduced into the chamber preferably via a device, in particular a spindle valve, as described above. The liquid sample is introduced into the chamber via a liquid inlet port in the chamber as described above.

Preferably, introducing in step a) is carried out in such a way that at most the entire lower region of the chamber, or at most the entire cavity formed by the lower region of the chamber, is filled with the liquid part or the liquid phase of the liquid sample. The lower region of the chamber therefore serves for receiving the entire liquid sample. The upper region of the chamber, on the other hand, remains free of liquid parts or liquid phases of the liquid sample, but instead only receives the components converted to the gas phase. This prevents liquid parts or liquid phase of the liquid sample from entering the gas phase outlet and thus entering the downstream analysis device. The volume of the liquid sample in the chamber is usually between 10 and 400 µl, preferably between 20 and 350 µl, more preferably between 30 and 300 µl. Accordingly, the lower region of the chamber, preferably shaped as a cone or truncated cone as described above, usually has a volume of 10 and 400 µl, preferably between 20 and 350 µl, more preferably between 30 and 300 µl.

Preferably, introducing of the liquid sample in step a) and of the gas phase in step c) is continuous. This means that the liquid sample is introduced in step a) and the gas phase is extracted in step c) without interruption.

In an alternative embodiment, introducing of the liquid sample in step a) and the extracting of the gas phase in step c) is effected in a clocked manner. "In a clocked manner" means that alternately a conversion interval follows an interruption interval. During the duration of the conversion interval, both introducing of the liquid sample in step a) and extracting of the gas phase in step c) take place. During the interruption interval, neither is the liquid sample introduced in step a) nor is the gas phase extracted in step c). The duration of the conversion interval may be the same as the duration of the interruption interval. Usually, the duration of the conversion interval is 1 second to 60 seconds, preferably 2 seconds to 50 seconds, and most preferably 3 seconds to 40 seconds, and the duration of the interruption interval is usually between 10 seconds and up to 24 hours, more preferably up to 12 hours, yet more preferably up to 1 hour, yet more preferably up to 30 minutes, yet more preferably up to 15 minutes, yet more preferably up to 5 minutes and most preferably up to 1 minute.

The partial conversion in step b) is effected at a temperature which is preferably in a range between 20° C. and 300° C., more preferably in a range from 25° C. to 275° C., more preferably in a range from 30° C. to 250° C., yet more preferably in a range from 35° C. to 225° C., yet more preferably in a range from 40° C. to 200° C., and most preferably in a range from 45° C. to 175° C. The temperature inside the chamber can be adjusted by one or more heating elements as described above.

The gas/liquid two-phase or multi-phase system in the chamber in step b) is preferably at least 90% in the equilibrium state, more preferably at least 93% in the thermodynamic equilibrium state, yet more preferably at least 96% in the thermodynamic equilibrium state, and most preferably at least 98% in the thermodynamic equilibrium state. "Equilibrium state" means the state that is created by the temperature given in the chamber. In other words, at a given temperature, an equilibrium between the liquid and gas phases of the component in the chamber is created for any component of the liquid sample after a certain time.

The creation of the equilibrium state in step b) is preferably done within a period of 0.5 s to 30 s, more preferably of 1 s to 20 s, yet more preferably of 2 s to 10 s, and most preferably of 3 and 8 s. Without wanting to be bound by theory, the duration of the creation of the equilibrium state in step b) does not only depend on the quantity or volume of the liquid sample present in the chamber. In the case of small quantities or small volumes of the liquid sample, for example 10 to 20 μl, the equilibrium state in step b) is usually reached within a short period, as indicated above. The duration also depends on the temperature difference of the liquid sample between the temperature the liquid sample has before being introduced into the chamber and the desired temperature to which the liquid sample is to be brought in the chamber, as described above. The larger this temperature difference is, the longer it usually takes to reach the equilibrium state. If, for instance, the liquid sample is introduced into the chamber at a temperature of 20° C. and the desired temperature is 30° C., the equilibrium in the chamber is usually reached within a short time, as indicated above, due to the small temperature difference.

Preferably, the gas phase is extracted from the chamber in step c) with a flow rate of 10 ml/min to 500 ml/min, more preferably of 20 ml/min to 450 ml/min, yet more preferably of 40 ml/min to 400 ml/min, yet more preferably of 60 ml/min to 300 ml/min, and most preferably of 100 ml/min to 200 ml/min. The gas phase is extracted from the chamber via a gas phase outlet port in the chamber, as described above.

Preferably the liquid phase of the gas/liquid two-phase or multi-phase system is extracted from the chamber through a liquid outlet port as described above. The extraction can be done by a pump, as described above.

On-Line Method

This invention also concerns a method for the on-line determination and analysis of components of a fluid sample comprising a plurality of components using a method for the partial conversion of a fluid sample comprising a plurality of components to the gas phase as described above in all embodiments.

All embodiments of the device according to the invention as described above in all embodiments are also preferred embodiments of the device used in the method according to the invention for on-line determination and analysis of components of a fluid sample comprising a plurality of components.

In particular, the heatable chamber of the method according to the invention is preferably designed as described above in all embodiments of the device. More preferably, a device comprising the heatable chamber as described above in all embodiments of the device is used in the method according to the invention for on-line determination and analysis of components of a liquid sample comprising a plurality of components.

All embodiments of the method for partial conversion of a liquid sample comprising a plurality of components to the gas phase as described above are also preferred embodiments of the method for on-line determination and analysis of components of a liquid sample comprising a plurality of components.

The above described advantages of the device according to the invention and the method according to the invention for partial conversion of a liquid sample comprising a plurality of components to the gas phase apply analogously to the method according to the invention for on-line determination and analysis of components of a liquid sample comprising a plurality of components.

Preferably, the liquid sample comprising a plurality of components is extracted from a process upstream to step a) or from a container upstream to step a). The liquid sample comprising a plurality of components may be extracted, for instance, from a reactor, a pipeline or a container of the process.

Preferably, the process upstream to step a) or the container is connected to the device by means of a fluid connection. The fluid connection preferably comprises a tube, a hose, a capillary or combinations thereof.

Preferably, the process upstream to step a) comprises a dilution process, more preferably an oil dilution process, in particular an engine oil dilution process, a solvent recovery process, a pharmaceutical process or a liquid waste process.

More preferably, the process upstream to step a) is a dilution process, more preferably an oil dilution process, in particular an engine oil dilution process, a solvent recovery process, a pharmaceutical process or a liquid waste process.

A pharmaceutical process, for instance, is a process for the production of drugs, especially liquid drugs.

Preferably, the ratio of the volume of the liquid phase of the liquid sample to the gas phase of the liquid sample in the chamber after the equilibrium in step b) has been reached and after optional dilution with diluent liquid and/or (carrier) gases as described above, is 1:150, more preferably 1:100.

Preferably, in step c) the extracted gas phase is introduced into a downstream analysis device. The device is preferably connected to the downstream analysis device by means of a fluid connection. The fluid connection preferably comprises a tube, a hose, a capillary or combinations thereof. The measurement period in the downstream analysis device for analysis and determination of the components contained in the extracted gas phase is usually 0.05 to 30 seconds, preferably 0.1 to 15 seconds.

Preferably, the downstream analysis device is a mass spectrometer as described above. In the mass spectrometer, all components present in the gas phase extracted in step c) can be determined qualitatively and quantitatively.

For the purposes of this application, average residence time means the time which the secondary component(s) of the liquid sample require(s) on average, or over time, from a particular first location or first step, for instance from extracting the liquid sample from the process upstream to step a), to a particular second location or second step, for instance introducing it into the analysis device downstream to step c).

Preferably, the average residence time of the components contained in the liquid sample between extracting the liquid sample from the process upstream to step a) and introducing it into the analysis device downstream to step c) is a maximum of 5 minutes, more preferably a maximum of 3 minutes and most preferably a maximum of 1 minute.

Preferably, the molecular weight of each of the components converted to the gas phase is a maximum of 500 Daltons, more preferably a maximum of 450 Daltons, yet more preferably a maximum of 400 Daltons. Components with a molecular weight of more than 500 Dalton are usually not converted to the gas phase at the temperatures applied in the method according to the invention or are converted to the gas phase in non-measurable concentrations. The concentration for any component converted to the gas phase is preferably between 1 ppb and 1000 ppb in the gas phase, more preferably between 5 ppb and 750 ppb, and most preferably between 10 ppb and 500 ppb.

In this application, ppb means "parts per billion", i.e. $10^{-9}$.

Preferably, after step c), the temperature of the extracted gas phase does not fall below the dew point of the components present in the gas phase. Thus, none of the components present in the gas phase condenses into their liquid state of aggregation, but the components reach the downstream analysis device in their gaseous state. The temperature may be prevented from falling below the set temperature by thermal insulation and/or heating of the fluid connection between the device and the downstream analysis device, for instance.

Preferably, the average residence time of between the introduction of the liquid sample into the chamber in step a) and the extraction of the gas phase of the two-phase or multi-phase gas/liquid system from the chamber in step c) is a maximum of 1 minute, more preferably a maximum of 45 seconds, and most preferably a maximum of 30 seconds. The average residence time is as defined above.

The fluid sample comprising a plurality of components preferably comprises one main component and one or several secondary components. The main component is in the liquid state before the liquid sample is introduced into the chamber of the device. The main component is preferably lubricating oil, engine oil, liquid waste, solvents and mixtures thereof.

Before the liquid sample is introduced into the chamber of the device, the one or several secondary components are preferably present in the liquid state of the liquid sample, or are present in the gaseous state and dissolved in the liquid main component.

The secondary component preferably comprises acetic acid, acetone, acetonitrile, anisole, benzene, 1-butanol, 2-butanol, butyl acetate, tert-butyl methyl ether, tetrachloromethane, chlorobenzene, trichloromethane, isopropyl benzene, cyclohexane, 1,2-dichloroethanes, 1-1-dichloroethene, 1,2-dichloroethene, dichloromethane, 1,2-dimethoxyethane, N,N-dimethylacetamide, N,N-dimethylformamide, dimethylsulfoxide, 1,3-dioxane, ethanol, 2-ethoxyethanol, ethyl acetate, ethylene glycol, ethyl ether, ethyl format, methanamide, methanoic acid, heptane, hexane, isobutyl acetate, isopropyl acetate, methanol, 2-methoxyethanol, methyl acetate, 3-methyl-1-butanol, methyl butyl ketone, methyl cyclohexanes, methyl ethyl ketone, methyl isobutyl ketone, 2-methyl-1-propanol, N-methyl pyrrolidone, nitromethane, pentane, T1-pentanol, 1-propanol, 2-propanol, propylacetate, pyridine, sulfolane, tetrahydrofuran, tetralin, toluene, 1,1,1-trichloroethane, 1,1,2-trichloroethene, triethylamine, xylene, butane, cyclopentane, octene or mixtures thereof.

The concentration of the main component in the liquid sample preferably is 85 wt. % or more, and the sum of all secondary components in the liquid sample is 15 wt. % or less. More preferably, the concentration of the main component in the liquid sample is 90% or more, and the sum of all secondary components in the liquid sample is 10 wt. % or less, yet more preferably, the concentration of the main component in the liquid sample is 92.5 wt. % or more, and the sum of all secondary components in the liquid sample is 7.5 wt. % or less, more preferably the concentration of the main component in the liquid sample is 95 wt. % or more, and the sum of all secondary components in the liquid sample is 5 wt. % or less, and most preferably the concentration of the main component in the liquid sample is 97.5 wt. % or more, and the sum of all secondary components in the liquid sample is 2.5 wt. % or less.

All of the above concentrations refer to the concentrations of the main and secondary component(s) in the liquid sample present in the chamber after optional introduction of a diluent liquid and/or after optional introduction of gases into the chamber as described above. If the concentration of the secondary components to be detected exceeds 15 wt. % in the liquid sample in the chamber, inaccuracies may occur in the quantitative determination of these secondary components in a downstream analysis device, for instance due to non-linearities. In order to remedy this, a diluent liquid may be introduced into the chamber through the further liquid inlet port by means of a flow rate control device, as described above. The diluent liquid is used to dilute the liquid sample in the chamber and is preferably the "zero substance" or main component of the liquid sample present in the chamber, as described above. This reduces the concentration of the secondary components to be detected in the liquid sample to 15 wt. % or less and avoids problems with the quantitative determination of these secondary components.

Use

The invention also relates to the use of the device according to the invention as described above in all embodiments as a sample treatment device in a method for the partial conversion of a liquid sample comprising a plurality of components to the gas phase, as described above in all embodiments.

The invention also relates to the use of the device according to the invention, as described above in all embodiments, as a sample treatment device in a method for on-line determination and analysis of components of a liquid sample comprising a plurality of components, as described above in all embodiments.

Further details, features and advantages of the subject-matter of the invention can be understood from the following description of the appendant figures, in which the preferred embodiments of the invention are illustrated.

Figure 2:
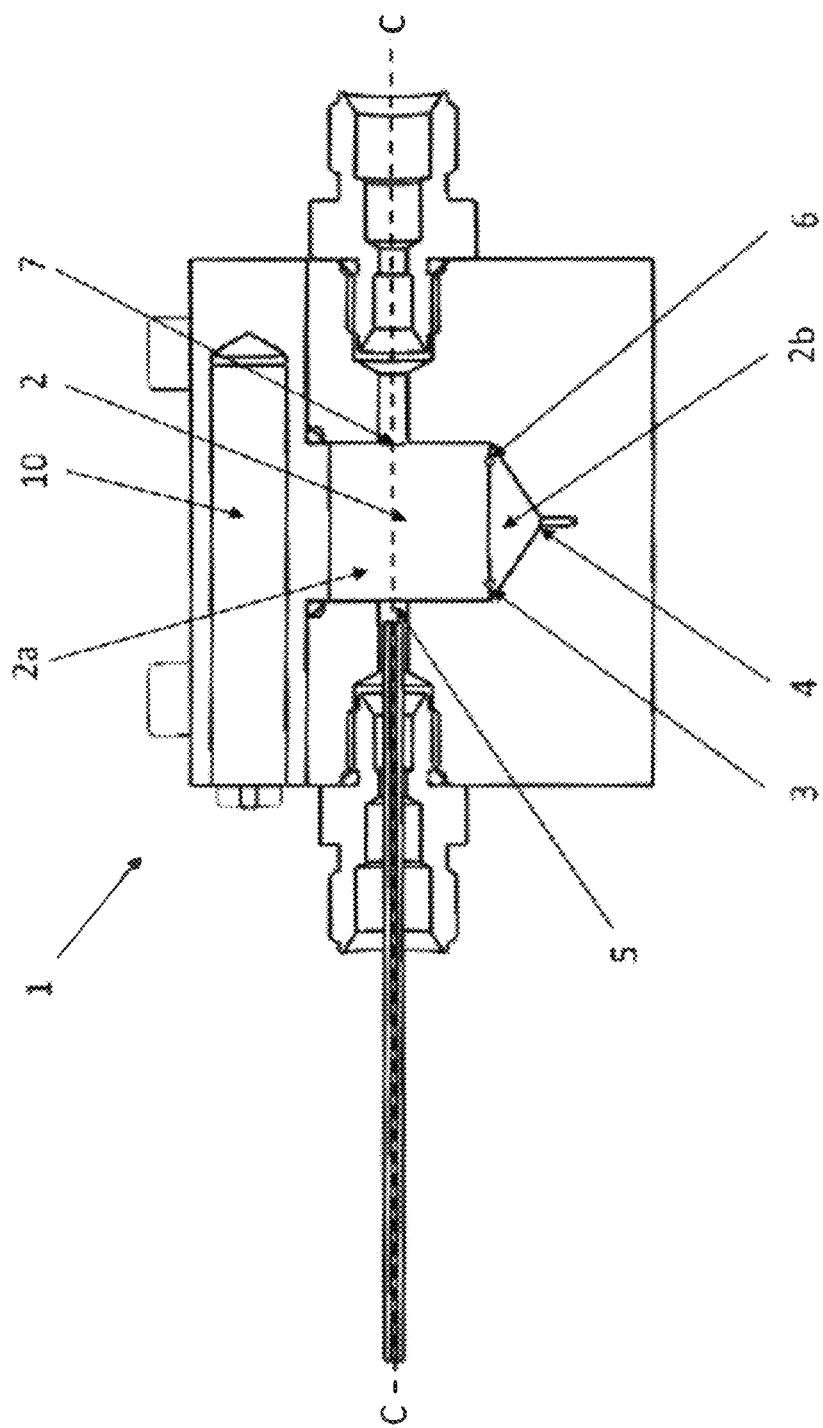
Figure 3:
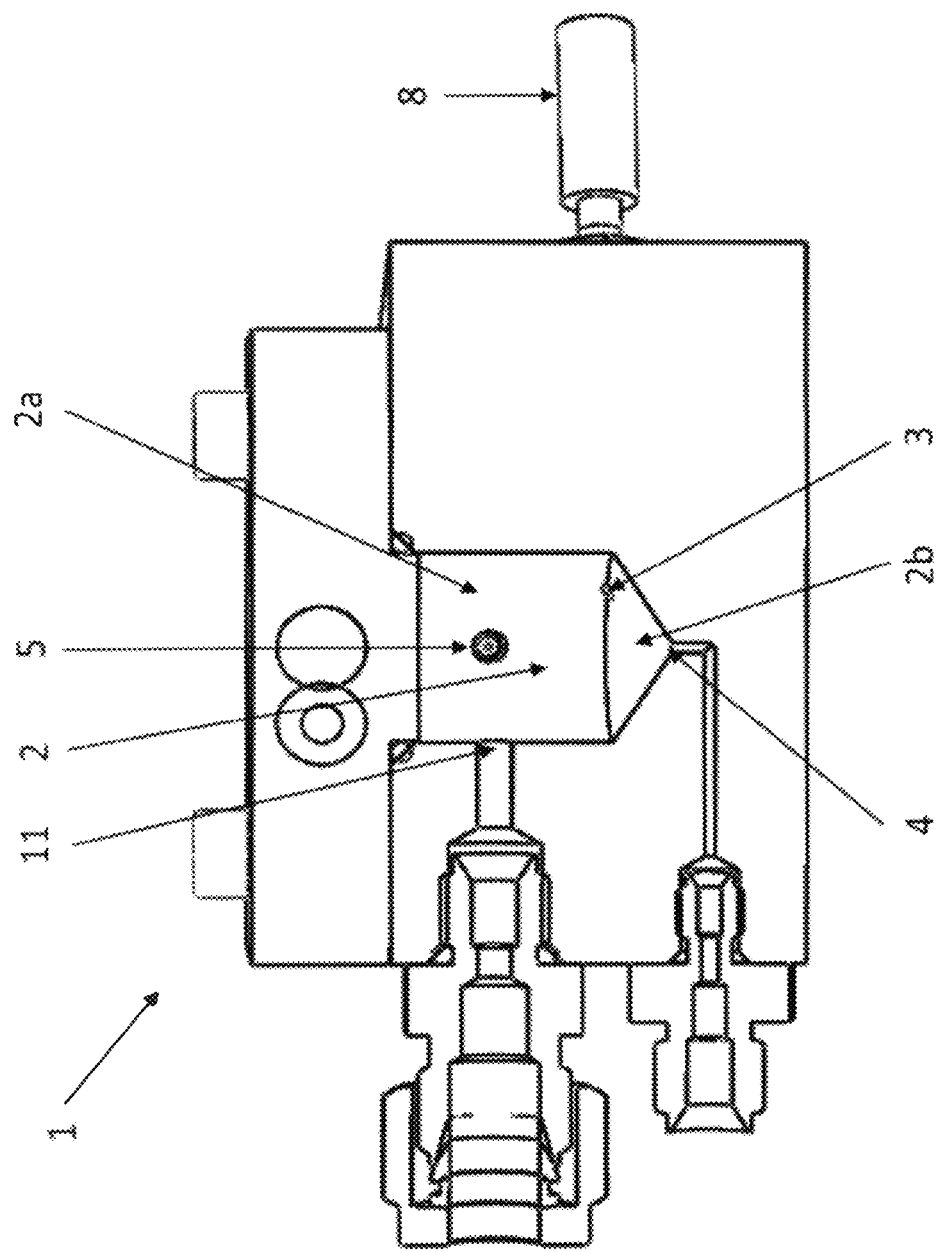
Figure 4:
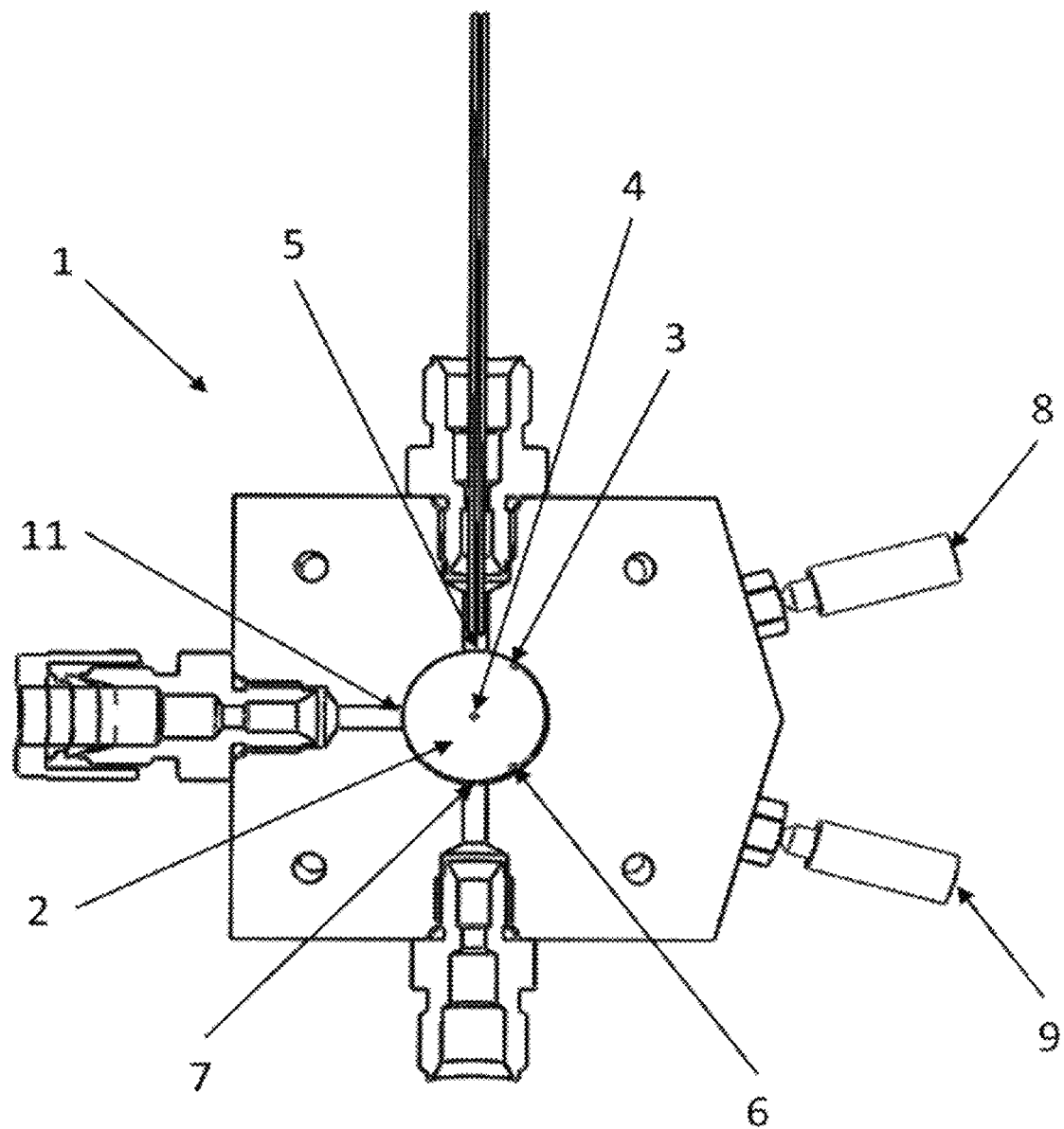
Figure 5:
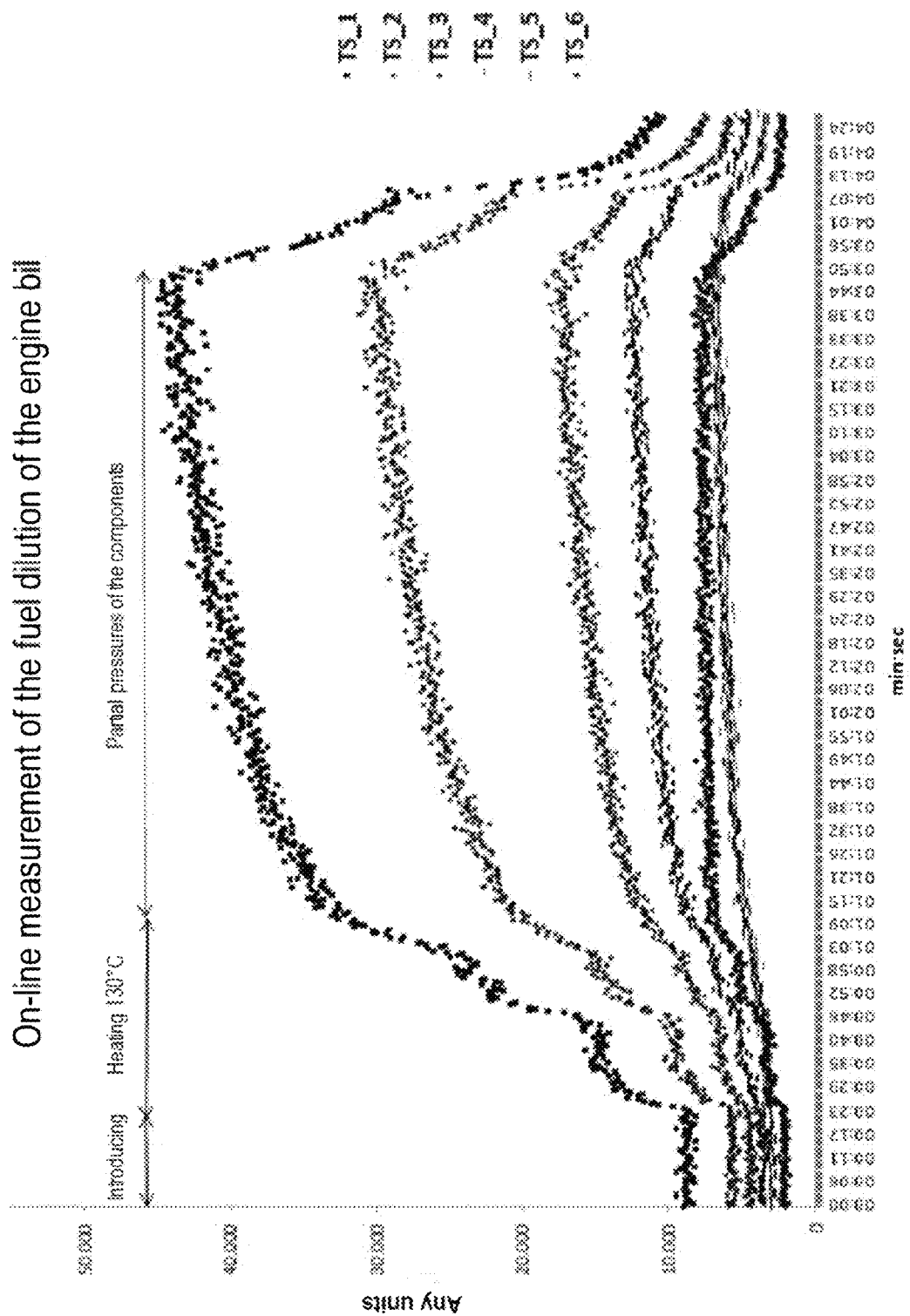
Figure 6:
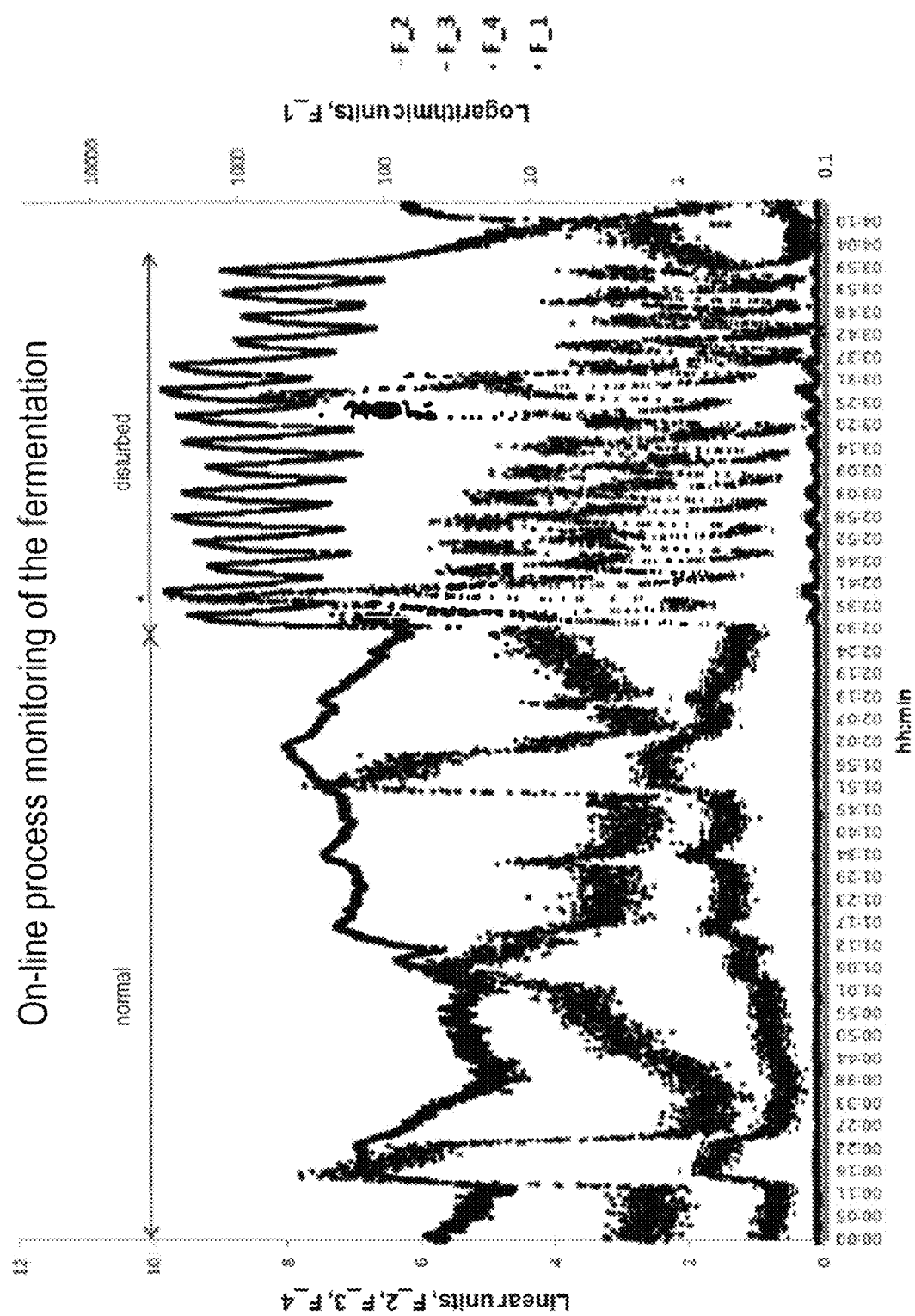

Shown are:

FIG. 1 an plan view of an embodiment of the device according to the invention for the partial conversion of a liquid sample comprising a plurality of components to the gas phase, FIG. 2 a cross-section through the device according to the invention along the line A-A in FIG. 1, FIG. 3 a cross-section through the device according to the invention along the line B-B in FIG. 1, FIG. 4 a cross-section through the device according to the invention along the line C-C in FIG. 2, FIG. 5 a measurement result of an on-line measurement of fuel dilution according to an embodiment of the method according to the invention, and FIG. 6 a measurement result of an on-line monitoring of a fermentation process according to an embodiment of the method according to the invention.

FIG. 1 shows a plan view of an embodiment of the device (1) according to the invention for the partial conversion of a liquid sample comprising a plurality of components to the gas phase. On the right side of the device (1), the device (8) for controlling the flow rate of the liquid sample into the liquid inlet port (3) and the device (9) for controlling the flow rate of the diluent liquid into the liquid inlet port (6) are arranged. In this exemplary embodiment, both devices (8, 9) are designed as spindle valves, by means of which the flow of the liquid sample or the diluent liquid into the chamber (2) can be controlled.

An outlet for carrier gas is arranged on the side of the device opposite the devices (8, 9).

A cross-section through the device according to the invention along the line A-A in FIG. 1 is shown in FIG. 2. The chamber (2) located inside the device (1) has an upper region (2a) and a lower region (2b) adjacent to the upper region (2a). The upper region (2a) has the shape of a straight circular cylinder, while the lower region (2b) has the shape of a straight cone, the liquid outlet port (4) being located at the tip of the cone. The diameter of the circular cylinder corresponds to the diameter of the circular base of the cone.

A heating element (10) is located above the upper region (2a) of the chamber (2) and heats the chamber via the walls delimiting the chamber, in particular those walls delimiting the upper region (2a) of the chamber (2), in such a way that the desired temperature is reached inside the chamber (2).

In the upper region (2a), the chamber (2) has a gas inlet port (7) for feeding gases into the chamber (2), and the gas phase outlet port (5) opposite the port (7). The gas phase outlet port (5) is connected to a capillary, as shown in FIG. 2, which in turn can be connected to an analysis device (not shown). As can also be seen from FIG. 2, both the port (7) and the port (5) are at the same height in the upper region (2a) of the chamber (2). The chamber (2) further has a liquid inlet port (3) for the inlet of the liquid sample into the chamber (2) and a liquid inlet port (6) for the introduction of a diluent liquid into the chamber (2). Both liquid inlet ports (3, 6) are arranged at the transition between the upper region (2a) and the lower region (2b) of the chamber (2). These two liquid inlet ports (3, 6) are used to fill the lower region (2b) of the chamber (2) with liquid sample or diluent liquid.

FIG. 3 shows a cross-section through the device according to the invention along the line B-B in FIG. 1. The gas outlet port (11) for the outlet of carrier gas from the chamber (2) is located at the same height in the upper region (2a) of the chamber (2) as the gas phase outlet port (5) for the outlet of the generated gas phase from the chamber (2). As already shown in FIG. 2, the liquid outlet port (4) for the discharge of liquid components not converted to the gas phase is located at the tip of the cone of the lower region (2b). FIG. 3 also shows the liquid inlet port (3) and the spindle valve (8) assigned to this inlet port.

FIG. 4 shows a cross-section through the device according to the invention along the line C-C in FIG. 2. In FIG. 4, it can be seen that the chamber (2) in this embodiment is arranged centrally in the device (1). As already shown in FIGS. 2 and 3, FIG. 4 also shows that the liquid outlet port (4) is centered at the bottom of the chamber (2). In FIG. 4, the liquid inlet ports (3, 6) with their associated valves (8, 9) can also be seen.

Example 1

Example 1 relates to the fuel dilution of engine oil and is provided to illustrate the principle of the method according to the invention for the on-line determination and analysis of components of a fluid sample comprising a plurality of components. Here, a device (1) according to the above example is used, as shown in FIGS. 1 to 4. An ion-molecule reaction mass spectrometer (IMR-MS; commercially available from V&F Analyse- and Messtechnik GmbH) is used for the determination of the components of the liquid sample to be converted to the gas phase. The liquid sample to be analysed is taken from an engine oil mixture of 20 ml diesel in 5 litres engine oil. In FIG. 5, the concentration curve of typical diesel hydrocarbons "TS1" to "TS6" over time is illustrated. TS1 to TS6 are long-chain, i.e. $C_{12}$ to $C_{16}$ hydrocarbons of diesel fuel. With reference to FIG. 5, at second 23 100 µl of the liquid sample is introduced into the chamber (2) of the device (1) via the liquid inlet port (3) with the spindle valve (8). Heating the liquid sample introduced into the chamber (2) from 40° C. to 130° C. takes about 1 minute. Subsequently, the components of the liquid sample which have been converted to the gas phase are transferred through the gas phase outlet port (5) of the device (1) by means of a capillary to the mass spectrometer for the determination and analysis of the gaseous components. The concentrations of the gaseous components are measured in the mass spectrometer from approx. 1 min 21 sec to 3 min 50 sec in FIG. 5. After the end of the measurement, the engine oil remaining in the chamber (2) is pumped out of the chamber (2) through the liquid outlet port (4) by a peristaltic pump.

Example 2

Example 2 is another application example of the method according to the invention for on-line determination and analysis of components of a fluid sample comprising a plurality of components. The method can not only be used for the determination and analysis of components, but it can also serve as a process monitoring system or process monitoring method. The on-line process monitoring is illustrated with the help of a fermentation process of maize, see FIG. 6. In example 2, the same device (1) including the mass spectrometer as in example 1 is used, wherein liquid samples of a fermentation process from the fermenter are continuously introduced into the device (1). The measured components F1 to F4 in FIG. 6, which are converted to the gas phase by means of a device (1), are characteristic compounds of the fermentation process that indicate the correct functioning of the plant or the fermentation process. Up to approx. 2 h 30 sec in FIG. 6, the fermentation process to be monitored runs normally. Subsequently, considerable fluctuations in the concentration of these characteristic components in the gas phase are detected, which indicates a disturbance in the process.

The two examples above are intended to demonstrate that the device according to the invention and the method according to the invention for on-line determination and analysis of components are suitable for monitoring continuous processes on-line, i.e. in "real time". In other words, disturbances in the processes to be monitored can be detected and diagnosed within a very short time, i.e. within a few minutes.

LIST OF REFERENCE SIGNS 1 device for the partial conversion of a liquid sample comprising a so plurality of components to the gas phase,
2 heatable chamber,
2a upper region of the chamber (2),
2b lower region of the chamber (2),
3 liquid inlet port for the inlet of the liquid sample into the chamber (2),
4 liquid outlet port for the discharge of liquid components from the chamber (2) which have not been converted to the gas phase,
5 gas phase outlet port for the outlet of the generated gas phase from the chamber (2),
6 liquid inlet port for introducing a diluent liquid into the chamber (2),
7 gas inlet port for feeding gases into the chamber (2),
8 device for controlling the flow rate of the liquid sample into the liquid inlet port (3), 9 device for controlling the flow rate of the diluent liquid into the liquid inlet port (6),
10 heating element,
11 gas outlet port for the outlet of carrier gas from the chamber (2)

The invention claimed is:

1. Device (1) for the partial conversion of a liquid sample comprising a plurality of components to the gas phase, comprising:
   (a) a heatable chamber (2) in which a two-phase or multi-phase gas/liquid system is produced, having
      (a1) a liquid inlet port (3) for the supply of the liquid sample,
      (a2) a liquid outlet port (4) for the discharge of liquid components from the chamber (2) which have not been converted to the gas phase, and
      (a3) a gas phase outlet port (5) for the discharge of the generated gas phase from the chamber; and
   (b) a device (6) for controlling the flow rate of the liquid sample into the liquid inlet port (3) from 1 µl/min to 3000 µl/min,
   characterised in that the chamber (2) has an upper region (2a) and a lower region (2b), the gas phase outlet port (5) being located in the upper region (2a) of the chamber (2); and
   wherein the lower region (2b) is connected to the upper region (2a), and wherein the upper region (2a) is in the shape of a solid of revolution of constant diameter and the lower region (2b) is in the shape of a solid of revolution of decreasing diameter; and
   and wherein the generated gas phase in the gas phase outlet comprises between 1 ppb and 1000 ppb converted gas components.

2. Device according to claim 1, wherein the chamber (2) has a volume of 0.1 to 25 cm³.

3. Device according to claim 1, the device (1) further comprising a device for controlling the gas phase flow from the chamber (2) from 10 ml/min to 500 ml/min.

4. Device according to claim 1, the device (1) further comprising a heating element (10), wherein heating of the chamber (2) is effected via the walls delimiting the chamber (2).

5. Device according to claim 1, wherein the chamber (2) comprises a further liquid inlet port (6) for inserting a diluent liquid, and/or wherein the chamber (2) further comprises a gas inlet port (7) for feeding carrier gases into the chamber (2) and/or a gas outlet port (11) for the discharge carrier gas from the chamber (2).

6. Method for the partial gas phase conversion of a liquid sample comprising a plurality of components, comprising the steps of
   a) introducing the liquid sample comprising a plurality of components into a heatable chamber (2) of a device (1),
   b) partially converting the liquid sample to the gas phase so that a gas/liquid two-phase or multi-phase system is created in the chamber (2) wherein the concentration of the components converted to the gas phase in step b) is between 1 ppb and 1000 ppb,
   c) extracting the gas phase of the gas/liquid two-phase or multi-phase system from the chamber (2) through a gas phase outlet port (5) of the chamber (2),
   characterised in that the chamber (2) has an upper region (2a) and a lower region (2b), wherein the gas phase outlet port (5) is located in the upper region (2a) of the chamber (2); and
   wherein the lower region (2b) is connected to the upper region (2a), and wherein the upper region (2a) is in the shape of a solid of revolution of constant diameter and the lower region (2b) is in the shape of a solid of revolution of decreasing diameter.

7. Method according to claim 6, wherein the partial conversion in step b) is effected at a temperature which is in a range between 20° C. and 300° C.

8. Method for on-line determination and analysis of components of a fluid sample comprising a plurality of components using the method according to claim 6.

9. Method according to claim 8, wherein the liquid sample comprising a plurality of components is extracted from a process upstream of step a) or from a container upstream of step a).

10. Method according to claim 9, wherein the average residence time of the components contained in the liquid sample between extracting the liquid sample from the process upstream of step a) and introducing into the analysis device downstream of step c) is a maximum of 5 minutes.

11. Method according to claim 9, wherein the molecular weight of any of the components converted to the gas phase in step b) is a maximum of 500 Daltons.

12. Method according to claim 9, wherein the liquid sample comprising a plurality of components comprises a main component and one or several secondary components, wherein the concentration of the main component in the liquid sample is 90 wt. % or more, and the sum of all secondary components in the liquid sample is 10 wt. % or less.

13. Method according to claim 8, wherein the gas phase extracted in step c) is introduced into a downstream analysis device.

14. Method according to claim 13, wherein the downstream analysis device is a mass spectrometer.

15. Method according to claim 8, wherein the introducing in step a) is carried out such that, at most, the lower region (2b) of the chamber (2) is filled with the liquid phase of the liquid sample.

16. Method according to claim 6, wherein the device (1) comprises:
   (a) the heatable chamber (2) in which a two-phase or multi-phase gas/liquid system is produced, having
      (a1) a liquid inlet port (3) for the supply of the liquid sample,
      (a2) a liquid outlet port (4) for the discharge of liquid components from the chamber (2) which have not been converted to the gas phase, and
      (a3) the gas phase outlet port (5) for the discharge of the generated gas phase from the chamber; and
   (b) a device (6) for controlling the flow rate of the liquid sample into the liquid inlet port (3) from 1 µl/min to 3000 µl/min.

17. Method for the partial gas phase conversion of a liquid sample comprising a plurality of components, comprising the steps of
   a) introducing the liquid sample comprising a plurality of components into a heatable chamber (2) of a device (1); comprising:
      (a) a heatable chamber (2) in which a two-phase or multi-phase gas/liquid system is produced, having
         (a1) a liquid inlet port (3) for the supply of the liquid sample,
         (a2) a liquid outlet port (4) for the discharge of liquid components from the chamber (2) which have not been converted to the gas phase, and
         (a3) a gas phase outlet port (5) for the discharge of the generated gas phase from the chamber; and (b) a device (6) for controlling the flow rate of the liquid sample into the liquid inlet port (3) from 1 µl/min to 3000 µl/min,
b) partially converting the liquid sample to the gas phase so that a gas/liquid two-phase or multi-phase system is created in the chamber (2), wherein the concentration of the components converted to the gas phase in step b) is between 1 ppb and 1000 ppb,
c) extracting the gas phase of the gas/liquid two-phase or multi-phase system from the chamber (2) through a gas phase outlet port (5) of the chamber (2),
wherein the device is characterized in that the heatable chamber (2) has an upper region (2a) and a lower region (2b), wherein the lower region (2b) is connected to the upper region (2a), and wherein the upper region (2a) is in the shape of a solid of revolution of constant diameter and the lower region (2b) is in the shape of a solid of revolution of decreasing diameter.

18. The device according to claim 1, wherein the upper region extends along a revolution axis and the lower region extends along the revolution axis.

\* \* \* \* \*